United States Patent
Kraskin et al.

[11] 4,099,976
[45] Jul. 11, 1978

[54] WATER-DISPERSIBLE BIODEGRADABLE COMPOSITIONS AND CONTAINERS AND THE LIKE MADE THEREFROM

[75] Inventors: Kenneth S. Kraskin, Milltown; Mohamed W. Hammad, Old Bridge, both of N.J.

[73] Assignee: Personal Products Company, Milltown, N.J.

[21] Appl. No.: 651,081

[22] Filed: Jan. 21, 1976

Related U.S. Application Data

[62] Division of Ser. No. 527,737, Nov. 27, 1974, Pat. No. 3,954,104.

[51] Int. Cl.² ............................. C08L 1/28; C09J 3/04
[52] U.S. Cl. ................................. 106/15 R; 106/194; 106/197 R; 128/263
[58] Field of Search ................. 106/15 R, 194, 183, 106/182; 128/263, 270

[56] References Cited

U.S. PATENT DOCUMENTS

| | | | |
|---|---|---|---|
| 2,979,410 | 4/1961 | Parlour | 106/15 R |
| 3,134,687 | 5/1964 | Lück | 106/15 R |
| 3,952,347 | 2/1976 | Comerford | 260/DIG. 43 |
| 3,954,104 | 5/1976 | Kraskin | 128/263 |

*Primary Examiner*—Theodore Morris
*Attorney, Agent, or Firm*—Jason Lipow

[57] ABSTRACT

A thermoplastic, water-dispersible, biodegradable composition of matter which is resistant to fungal attack prior to dispersal, and containers and the like made therefrom. The composition comprises hydroxyalkyl cellulose, starch, and a member selected from the group consisting of sorbic acid and its alkali metal salts as the anti-fungal agent. Only a member of this group is found to be an effective anti-fungal agent in the composition of the invention.

14 Claims, 2 Drawing Figures

U.S. Patent July 11, 1978 4,099,976
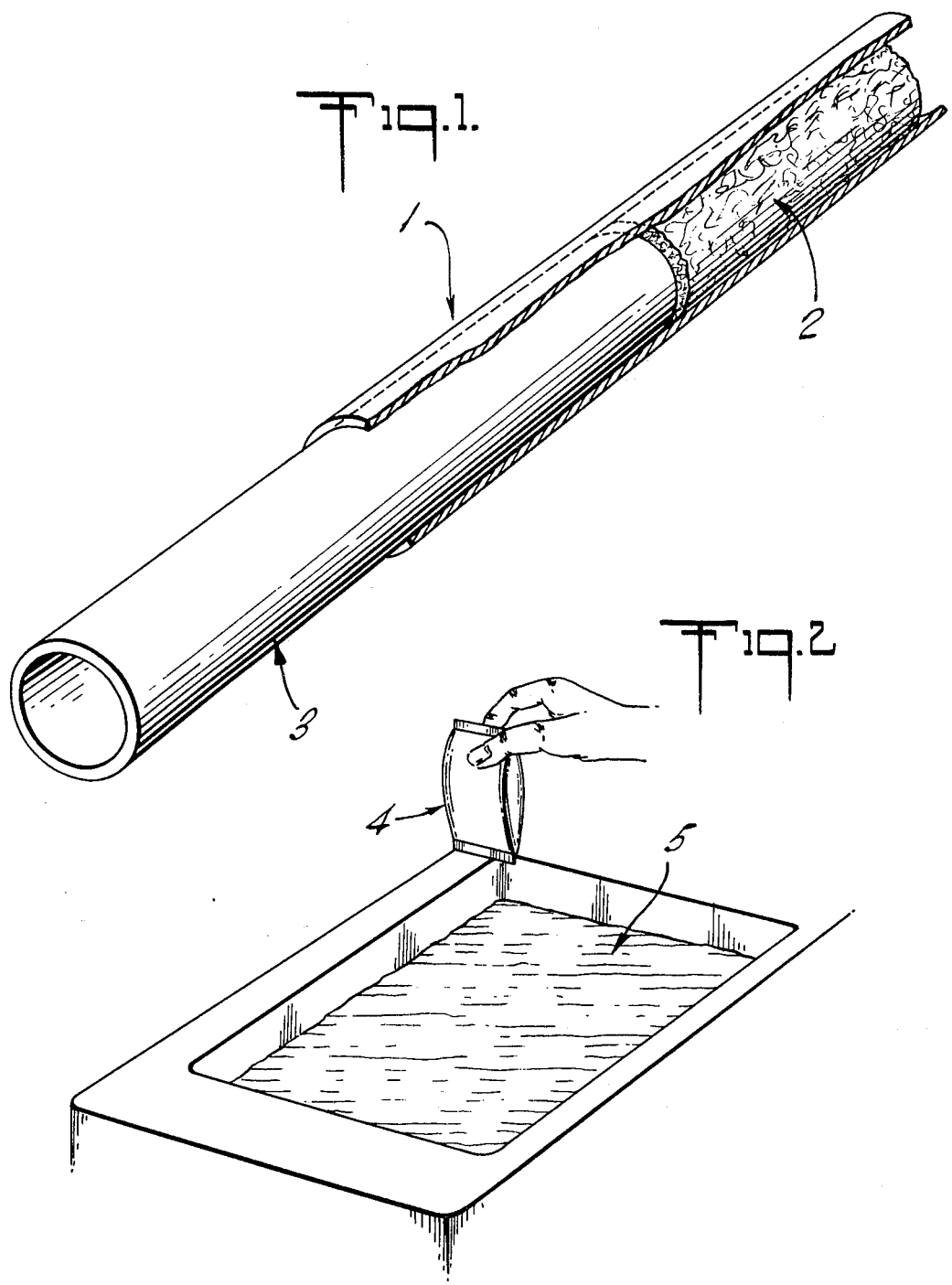

WATER-DISPERSIBLE BIODEGRADABLE COMPOSITIONS AND CONTAINERS AND THE LIKE MADE THEREFROM

This is a division of application Ser. No. 527,737 filed Nov. 27, 1974 now U.S. Pat. No. 3,954,104.

BACKGROUND OF THE INVENTION

This invention relates to water-dispersible, biodegradable compositions of matter and to containers and the like made therefrom. More particularly, the invention relates to such compositions of matter which are resistant to fungal attack prior to dispersal and to containers and the like made therefrom.

Such containers are suitable for many diverse uses, for example, toilet-disposable catamenial tampon applicators, containers for patient laundry in a hospital, packets for addition of premeasured amounts of ingredients to aqueous fluids, and the like. Containers made from the composition of the invention are suitable for these uses because they are resistant to fungal attack prior to disposal in water or an aqueous solution, yet are biodegradable once disposed.

Water-dispersible compositions of matter are known which combine a water-insoluble, nonbiodegradable filler, such as talc, and a water-soluble, thermoplastic polymer, such as hydroxypropyl cellulose. Such compositions will disintegrate in an excess of water when the water-soluble polymer dissolves, leaving the water insoluble, nonbiodegradable filler dispersed therein. Hanke, U.S. Pat. No. 3,724,462, teaches that such filled compositions are superior to unfilled thermoplastic polymers in the manufacture of catamenial tampon applicators because they maintain their shape better under conditions of high humidity and temperature, are less likely to fuse together or adhere to the tampon under such conditions, and are much less expensive then unfilled thermoplastic polymers. A tampon applicator made according to the teaching of Hanke is toilet-disposable because of its water-dispersibility. The disadvantage with such compositions is, of course, that the filler is both insoluble and nonbiodegradable and hence accumulates wherever the composition is dispersed. Thus, if the composition is flushed in a water closet, the filler accumulates in the toilet or sewage system. Such a composition is also generally not suitable for the manufacture of containers designed for the addition of premeasured amounts of ingredients to aqueous fluids because the insoluble filler would accumulate therein, which is undesirable. Uses where the accumulation of such a nonbiodegradable filler would be disadvantageous are, for example, the addition of flavorings or colorings to food or the addition of soaps to detergents to laundry. The presence of, for example, talc in such as food or laundry is unacceptable.

The provision of a completely biodegradable, water-dispersible, filled composition has been an object which has so far eluded the art. Such a composition must be completely biodegradable after dispersal, yet must not be susceptible to attack by micro-organisms, particularly fungi, prior to dispersal (e.g., while in storage). These apparently contradictory objects of long shelf life and readily biodegradability have not yet been achieved in a single filled composition.

SUMMARY OF THE INVENTION

In accordance with the present invention, there is disclosed a thermoplastic, water-dispersible, biodegradable composition of matter which is resistant to fungal attack prior to dispersal, and containers and the like made therefrom. Objects made of the composition of the invention are not susceptible to fungal attack during storage or use, but yet are completely biodegradable when dispersed in an excess of water or aqueous fluid, as for example in a septic system.

The composition of the invention comprises hydroxyalkyl cellulose, starch, and a member selected from the group consisting of sorbic acid and its alkali metal salts as an anti-fungal agent. The hydroxyalkyl cellulose is a biodegradable, thermoplastic polymer selected to be water-soluble and should be present in a proportion sufficient to make the composition water-dispersible and thermoplastic. The starch is a biodegradable filler and should be present in a proportion sufficient to effect the advantages which obtain from filling the polymer, i.e., rigidity, little effect of high humidity, and low cost. While it is economically advantageous to have the proportion of starch to hydroxyalkyl cellulose as large as possible consistent with the desired use thereof, it should be understood that any proportion of starch below such upper limit is contemplated to be within the scope of the invention.

The sorbic acid or alkali metal sorbate must be present in an antimycotically-effective amount.

While sorbic acid and its alkali metal salts are well-known as several of a large number of antimycotic agents used in food and other products, the most surprising aspect of the present invention is that only sorbic acid and the alkali metal salts thereof are found to be antimycotically effective in the composition of the present invention. This unobvious result is contrary to the express teachings of the prior art that sorbic acid is but one of a large class of antifungal agents as disclosed, for example, in U.S. Pat. No. 2,379,294. By the term "alkali metal salts" I mean to include lithium sorbate, sodium sorbate, potassium sorbate, rubidium sorbate, and cesium sorbate.

DETAILED DESCRIPTION OF THE INVENTION

While it is contemplated that any hydroxyalkyl cellulose which is water-soluble, thermoplastic, and has a melting point well below the decomposition temperature of starch (so as to be moldable) would be suitable in the composition of the invention, such as, for example, hydroxymethyl cellulose, hydroxyethyl cellulose, hydroxypropyl cellulose, hydroxybutyl cellulose, and the like, the preferred hyroxyalkyl cellulose is hydroxypropyl cellulose, and more specifically is that hydroxypropyl cellulose sold by Hercules Corporation under the trademark KLUCEL GF, which is a nonionic, water-soluble, cellulse ether having a molecular weight of approximately 300,000 and a molar substitution of from about 3 to about 5.

A wide variety of starches are useable in the composition of the invention, as for example wheat starch, corn starch, or tapioca starch. Corn starch having an amylose content of from about 22% to about 28% and an average granule size of from about 5 microns to about 26 microns is preferred.

While the proportion of starch to hyroxyalkyl cellulose may vary greatly so long as it is not as great as to make the composition brittle and unsuitable for containers and the like, the preferred range for this proportion is from about 1.5 to about 2.5 times by weight as much starch as hydroxyalkyl cellulose. The weight of starch should not exceed about three times the weight of hydroxyalkyl cellulose if the composition is to be used for containers and the like to avoid undesirable brittleness for that use. It is contemplated, however, that this brittleness might not be undesirable in other uses and hence, a composition comprising a greater proportion of starch might be used.

Because of this problem a fungal attack on the biodegradable starch component of this composition, there is admixed therein an antimycotically-effective amount of a member selected from the group consisting of sorbic acid and its alkali metal salts. That only a member selected from this group, of all the antimycotic agents tested, is found to be effective in preventing fungal growth on the composition of this invention while not hindering its later biodegradability is a surprising and unexpected result. Not all members of this group are identically effective in preventing fungal growth under all conditions. Specifically, if the composition is exposed immediately to high relative humidity (80–90%) after being innoculated with the test fungus, only sorbic acid is effective in preventing fungal growth. If, on the other hand, the innoculated composition is incubated under conditions of normal relative humdidity (40–50%) prior to its exposure to high humidity, all members of the group are effective. While Applicants have no definite explanation for this surprising result, it seems likely that a period of normal humidity incubation permits the alkali metal sorbate to react in some fashion with the composition so that it becomes antimycotically effective.

Because most products made from the composition of the invention (e.g., tampon applicators) will be stored under normal humidity conditions (in an assembly plant, for example) prior to being exposed to high humidity conditions, all members of the group will be effective in such products.

If sorbic acid is used as the antimycotic agent, it must comprise more than about 0.05% by weight of the composition to be effective. If potassium sorbate is used, it must comprise more than about 0.1% by weight of the composition to be effective. Amounts of sorbic acid and potassium sorbate up to about 3% by weight have been found antimycotically-effective without deterring the later biodegradability of the composition. While amounts of antimycotic agent within these ranges are therefore preferred, it should be understood that it is within the scope of the present invention to admix in the composition of the invention any antimycotically effective amount of the above described agents, so long as biodegradability of the resulting composition is not hindered. More preferred is at least 0.1% by weight sorbic acid and most preferred is at least 0.2% by weight sorbic acid.

The composition of the invention may further comprise lubricants to facilitate the manufacture of containers and the like therefrom, an antioxidant, and an opacifying agent. The preferred lubricants are lauryl thiodipropionate, glycerol monostearate, and various polyalkylene glycols, such as polyethylene glycol, polypropylene glycol, and the like, sold by Union Carbide Corporation under the tradename CARBOWAX. The specific CARBOWAX materials used are denominated CARBOWAX 400 (average molecular weight 380–420, specific gravity 1.13) and CARBOWAX 4000 (average molecular weight 3,000–3,700, specific gravity 1.204). The preferred antioxidant is butylated hydroxytoluene or ditertbutyl-para-cresol sold by Hercules Corporation under the trademark DELPAC R. Further, titanium dioxide or other suitable material may be added to the composition to render it opaque to visible light.

The composition of the invention may be used to make containers and the like which are desired to be water-dispersible and biodegradable when dispersed, while also being resistant to fungal attack prior to dispersal. Because the solubility of certain hydroxyalkyl cellulose materials is dependent upon temperature, these materials being soluble in cold water (below about 40° C) but not in hot water (above about 40° C), it should be understood that the compositions of the invention comprising these hydroxyalkyl celluloses are not suitable for use with hot water. Specifically, compositions containing KLUCEL GF hydroxypropyl cellulose should preferably not be used with hot water.

One type of use envisioned for the composition of the invention is to contain premeasured ingredients for addition to aqueous liquids, so that the entire packet may be added. The container will disintegrate upon addition to the liquid, thus releasing the ingredients. Examples of such a use are packets of industrial food ingredients, such as colorings or flavorings, packets of cosmetics, such as hair dye or bath salts, packets of laundry products, such as soaps or cleansers, and the like. The composition of the invention may be used to form ingestable capsules for drugs, vitamins and the like.

A second type of use for which the composition of the invention is well suited is a container for patient laundry in a hospital. Such laundry must be contained after removal from the patient to prevent the spread of disease within the hospital and to protect those who process the laundry. Containers made from the composition of the invention are ideal to withstand fungal attacks in the warm, moist environment generated by the laundry, while also depending completely upon the laundry-containing bundle is immersed in wash water. The bundle may be immersed in the wash water without the necessity of removing the laundry therefrom, thereby making the washing a safer and more efficient process.

A particularly important use of the composition of the present invention is to make flushable, biodegradable, catamenial tampon applicators. These applicators possess the advantages of prior art applicators manufactured from filled thermoplastic compositions of matter, while in addition being both disposable in a sewage system and yet resistant to fungal attack prior to disposal. An applicator manufactured according to the present invention may be of any conventional type, but the tube type is preferred. The particular form of the tampon applicator comprises no part of the present invention. The applicator of the invention may be manufactured by any conventional technique applicable to thermoplastic materials, such as extrusion, molding, and the like.

IN THE FIGURES

FIG. 1 is a perspective view of a tampon applicator and a tampon with parts broken away. The embodiment shown in the Figure comprises outer tube 1 made of the composition of the invention, having tampon 2 movably received within one end thereof and plunger 3 movably received within the other end thereof. The tampon containing end of the applicator is inserted into the body cavity and the tampon is expelled therefrom by the pressure of the plunger. This plunger may be made of any substantially rigid, biodegradable material, including the composition of the invention.

FIG. 2 is a perspective view of a water-dispersible biodegradable container in use. The embodiment shown in the Figure comprises container 4 made of the composition of the invention, contained within which is a food ingredient, laundry product, or the like. The container is about to be immersed in aqueous liquid 5, whereupon it will disintegrate to release its contents into the liquid.

The present invention will be further described by the following examples.

EXAMPLE I

Three compositions of matter were prepared according to the present invention with the quantities and ingredients set forth in the following table:

TABLE 1

| Components: | % by Weight | | |
|---|---|---|---|
| | Wheat Starch | Tapioca Starch | Corn Starch |
| Starch | 61.19 | 61.16 | 62.28 |
| KLUCEL GF | 26.22 | 26.22 | 26.69 |
| Titanium dioxide | 1.75 | 1.75 | 1.78 |
| Delpac R | .18 | .18 | .18 |
| Lauryl Thiodipropionate | .18 | .18 | .18 |
| Glycerol Monostearate | 1.75 | 1.75 | 1.78 |
| Carbowax 400 | 2.62 | 2.62 | 4.45 |
| Carbowax 4000 | 6.12 | 6.12 | 2.67 |

The components of each composition were thoroughly mixed together at a temperature of about 150° C until a homogeneous composition was formed. These three compositions were then tested as indicated in the following examples.

EXAMPLE II

Tampon applicators each comprising a hollow tube made from one of the compositions of Example I and a cardboard plunger were each fitted with a tampon (manufactured by Personal Products Company under the trademark MODESS). Two sizes of applicators were made to accomodate "Regular" and "Super" tampons. The tampon-containing applicators were then individually wrapped in paper wrappers and placed in a cardboard box. Each box was wrapped in a heat-shrink cellophane wrapper and then overwrapped with a heat-shrink polypropylene film. These individual boxes were then placed in a corrugated case and sealed. The cases were placed in a circulating air chamber controlled at 60° C ± 2° C and 85% ± 5% relative humidity for 24 hours. After this aging, the force required to expel five of each size tampon from each type of applicator was determined. The results are given in the following table and data from ten tests of polyethylene applicators of identical design are also given for comparison.

TABLE 2

| | Expulsion Force after Aging (Ounces) | | | |
|---|---|---|---|---|
| | Wheat Starch* | Tapioca Starch* | Corn Starch* | Polyethylene** |
| Regular | 35.4 | 27.5 | 17.7 | 34.3 |
| (Range) | (30–42) | (19–36) | (11–35) | (28–51) |
| Super | 35.0 | 52.6 | 25.0 | 33.9 |
| (Range) | (27–40) | (51–54) | (18–31) | (24–44) |

*average of five tests
**average of ten tests

The results indicate that the composition containing corn starch required the lowest explusion force. Therefore, it is the preferred composition for tampon applicators because of the relative ease with which it expels a tampon for insertion in the vaginal chamber.

EXAMPLE III

Applicator tubes made of each of the three compositions of Example I were suspended in still distilled water. The applicator tubes were then observed over time and the degree of disintegration was noted. All applicator tubes substantially dispersed in 2.5 hours; there were no observable differences in the disintegration rates of the three compositions. In agitated water, as for example in a water closet or sewage system, disperson would of course be considerably more rapid.

EXAMPLE IV

Applicators prepared from the preferred corn starch containing composition of Example I which had been admixed with from 0.05% to 1.0% of a member selected from the group consisting of sorbic acid and potassium sorbate were surface innoculated with $200 \times 10^3$ *Penicillium conidia* (spores). The innoculated samples were then maintained at normal room humidity (40–50% relative humidity) for 14 days before being transferred to a high humidity chamber (80–90% relative humidity) for seven days. The degree of inhibition of fungal growth is indicated in the following table.

TABLE 3

| Applicator Sorbic Acid Content | Fungus Growth (7 Days) |
|---|---|
| None | + |
| 0.05% Sorbic Acid | + |
| 0.1% Sorbic Acid | 0 |
| 0.5% Sorbic Acid | 0 |
| 1.0% Sorbic Acid | 0 |
| Potassium Sorbate Content | |
| None | + |
| 0.05% Potassium Sorbate | + |
| 0.1% Potassium Sorbate | + |
| 0.2% Potassium Sorbate | 0 |
| 0.5% Potassium Sorbate | 0 |

+ = Heavy Fungus Growth
O = No Fungus Growth

Note that while 0.05% by weight sorbic acid was ineffective in preventing fungal growth, 0.1% by weight sorbic acid was effective; potassium sorbate at concentrations of greater than 0.1% was effective.

EXAMPLE V

Applicators containing various amounts of antimycotic agents admixed with the preferred corn starch-containing composition of Example I were tested according to the procedure of Example IV except that the applicators were not maintained at normal room humidity for any period, rather they were directly incubated at 80 to 90% humidity and 28° to 30° C for seven days. Samples were examined for fungus growth following the high humidity incubation. The degree of fungal inhibition by various agents and various levels of agents is shown in the following table.

TABLE 4

| | Fungal Inhibition by Various Levels of Agent | |
|---|---|---|
| | 0.1% | 0.5% |
| Untreated | + | + |
| Sodium Propionate | + | + |
| Propyl paraben | + | + |
| Sorbic Acid | 0 | 0 |

TABLE 4-continued

| | Fungal Inhibition by Various Levels of Agent | |
|---|---|---|
| | 0.1% | 0.5% |
| Potassium sorbate | + | + |

+ = Fungus Growth
0 = No Fungus Growth

Note that only sorbic acid of all the agents tested was effective; potassium sorbate alone or in combination with methyl or propyl paraben was not effective under the conditions of this test.

EXAMPLE VI

The biodegradability of applicators manufactured from the preferred corn starch-containing composition containing sorbic acid was studied using the following procedure. Anaerobic digester units composed of sealed glass bottles fitted with gas exhaust tubes whereby the gas expelled by the unit can be measured were prepared containing about 700 to 800 ml. of anaerobic digested sludge to which fresh raw sewage had been added. Test samples of 1.5 grams of the preferred corn starch composition of Example 1 containing about 0.2% by weight sorbic acid were added and the units were sealed. Identical control units were also prepared without test samples. The gas produced by degradation was collected and measured daily and samples were removed weekly to determine the extent of actual solids degradation. Gas production was initiated rapidly and maintained at a vigorous rate in the composition-containing digesters, thus suggesting rapid digestion of the starch component of the composition. The materials were readily attacked and required no period of acclimatization. Examination of the solid material after a twenty-eight day test period revealed that 58% of the volatile solids of the applicator composition were destroyed during this period. The residual material was totally soluble and was not detected by gross examination of the sewage sludge.

While the composition of the invention has been exemplified primarily in the manufacture of applicators for catamenial tampons, it should be understood that the scope of its utility is much wider. It is intended that this composition may be used to form any sort of container or the like which is desired to be water-dispersible and biodegradable, while at the same time being resistant to fungal attack prior to dispersal.

As many widely different embodiments of this invention may be made without departing from the scope thereof, it is to be understood that the invention is not limited to the specific embodiments thereof except as defined in the appended claims.

What is claimed is:

1. A thermoplastic, water-dispersible, biodegradable composition of matter comprising hydroxyalkyl cellulose, starch, and an antimycotically-effective amount of a member selected from the group consisting of sorbic acid and its alkali metal salts, whereby the composition is biodegradable after disposal but resistant to fungal attack prior to dispersal.

2. A composition of matter as in claim 1 wherein the weight ratio of starch to hydroxyalkyl cellulose in the composition is from about 1.5 to about 2.5.

3. A composition of matter as in claim 1 wherein the hydroxyalkyl cellulose is hydroxypropyl cellulose.

4. A composition of matter as in claim 3 wherein the hydroxypropyl cellulose has a molecular weight of about 300,000 and a molar substitution of from about three to about five and the starch is corn starch, and wherein the weight ratio of starch to hydroxypropyl cellulose in the composition is from about 1.5 to about 2.5.

5. A composition of matter as in claim 2 which comprises at least about 0.1% by weight sorbic acid.

6. A composition of matter as in claim 2 which comprises at least about 0.2% by weight potassium sorbate.

7. A composition of matter as in claim 3 which comprises at least about 0.1% by weight sorbic acid.

8. A composition of matter as in claim 3 which comprises at least about 0.2% by weight potassium sorbate.

9. A composition of matter as in claim 4 which comprises at least about 0.1% by weight sorbic acid.

10. A composition of matter as in claim 4 which comprises at least about 0.2% by weight potassium sorbate.

11. A composition of matter as in claim 9 which further comprises a lubricant, an antioxidant, and an opacifying agent.

12. A container consisting essentially of the composition of claim 1.

13. A container consisting essentially of the composition of claim 4.

14. A container consisting essentially of the composition claim 9.

* * * * *